(12) United States Patent
Zhao et al.

(10) Patent No.: US 11,124,758 B2
(45) Date of Patent: Sep. 21, 2021

(54) BACTERIA CULTURE MEDIUM AND APPLICATIONS THEREOF

(71) Applicant: SHANGHAI PROMOTON BIOTECHNOLOGY CO., LTD., Shanghai (CN)

(72) Inventors: Botao Zhao, Shanghai (CN); Chunhai Cai, Shanghai (CN); Guoquan Zhou, Shanghai (CN); Dehua Yang, Shanghai (CN); Jin Liu, Shanghai (CN)

(73) Assignee: SHANGHAI PROMOTON BIOTECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 14/893,275

(22) PCT Filed: Oct. 15, 2013

(86) PCT No.: PCT/CN2013/085254
§ 371 (c)(1),
(2) Date: Nov. 23, 2015

(87) PCT Pub. No.: WO2015/021692
PCT Pub. Date: Feb. 19, 2015

(65) Prior Publication Data
US 2016/0097030 A1    Apr. 7, 2016

(30) Foreign Application Priority Data
Aug. 13, 2013 (CN) .......................... 201310351748.1

(51) Int. Cl.
*C12N 1/20* (2006.01)
*A61K 31/43* (2006.01)
*A61K 31/546* (2006.01)

(52) U.S. Cl.
CPC .............. *C12N 1/20* (2013.01); *A61K 31/43* (2013.01); *A61K 31/546* (2013.01); *C12N 2500/30* (2013.01)

(58) Field of Classification Search
CPC ...... C12N 1/20; C12N 2500/30; A61K 31/43; A61K 31/546
See application file for complete search history.

(56) References Cited

U.S. PATENT DOCUMENTS

| 2,725,336 | A | | 11/1955 | Sumner et al. | |
|---|---|---|---|---|---|
| 3,351,527 | A | * | 11/1967 | Apat ..................... | A61K 9/0019 424/497 |
| 4,172,138 | A | * | 10/1979 | Rhodes ................ | A61K 9/0041 514/199 |
| 2010/0047852 | A1 | * | 2/2010 | Ford .......................... | C12N 1/20 435/34 |
| 2016/0097030 | A1 | | 4/2016 | Zhao et al. | |

FOREIGN PATENT DOCUMENTS

| CA | 854698 | 10/1970 |
|---|---|---|
| CN | 1517090 | 8/2004 |
| CN | 101721366 | 9/2011 |
| CN | 101884633 | 7/2012 |
| CN | 103230366 | 8/2013 |
| CN | 103396968 | 3/2015 |
| EP | 3018134 | 4/2018 |
| FR | 2973042 | 9/2017 |
| NZ | 258199 | 1/1997 |

OTHER PUBLICATIONS

Essential Medicines and Health Products Information Portal, A World Health Organization (WHO hereinafter) Resource available at http://apps.who.int/medicinedocs/en/d/Jh2918e/23.2.html.*
Parker et al. (Journal of Pharmacy and Pharmacology vol. 6, Issue 1, pp. 167-170).*
Santa Cruz Biotechnology Inc. (hereinafter Santa Cruz), Material Safety Data Sheet for Penicillin G benzathine salt hydrate, pp. 1-7, PDF downloaded at http://datasheets.scbt.com/sc-228904.pdf Issue Date: Sep. 13, 2009, Print Date Nov. 23, 2010.*
Abraham et al., "An enzyme from bacteria able to destroy penicillin," Nature (1940) 146(4):837-838.
Ambler et al., "The structure of beta-lactamases," Philos Trans R Soc. Lond B (1980) 289(1036):321-331.
Bush et al., "A functional classification scheme for beta-lactamases and its correlation with molecular structure," Antimicrob Agents Chemother (1995) 39(6):1211-1233.
Bush et al., "Updated functional classification of beta-lactamases," Antimicrob Agents Chemother (2010) 54(3):969-976.
Concannon et al., "Stability of aqueous solutions of amoxicillin sodium in the frozen andliquidstates," Am J Hosp Pharm (1986) 43(12):3027-3030.
Datta et al., "Penicillinase synthesis controlled by infectious R factors in Enterobacteriaceae," Nature (1965) 208(5007):239-241.
International Search Report and Written Opinion for PCT/CN2013/085254, dated Apr. 17, 2014.
Medeiros et al., "Evolution and dissemination of beta-lactamases accelerated by generations of beta-lactam antibiotics," Clin Infect Dis (1997) 24 Suppl 1: s19-45.
Novagen, "pET System Manual TB055 11th Edition User Protocol." 2011.

(Continued)

*Primary Examiner* — Blaine Lankford
(74) *Attorney, Agent, or Firm* — Morrison & Foerster LLP

(57) ABSTRACT

The present invention has publicized a bacteria culture medium. In common bacteria culture medium, one kind or several kinds of β-lactam antibiotics and/or the salts thereof were premixed. The β-lactam antibiotics and/or the salts thereof premixed in the bacteria culture medium is slightly soluble in water at 25° C. and the solubility is less than 10 mg/ml. The concentrations of the β-lactam antibiotics premixed in the culture medium are greater than the solubility of the used β-lactam antibiotics at 25° C., but are less than 100 mg/ml. The bacteria culture medium can be used to selectively culture bacteria with β-lactam antibiotic resistance and can be stored for a long time.

14 Claims, No Drawings

(56) References Cited

OTHER PUBLICATIONS

Public Release Summary on Evaluation of the new active CEPHAPIRIN in the product/s MetricureBenzathinecephapirin intra-uterine suspension. National Registration Authority for Agricultural and Veterinary Chemicals of Australia (2001).
Savello et al., "Stability of sodium ampicillin solutions in the frozen andliquidstates," Am J Hosp Pharm (1971) 28(10):754-759.
Deshpande, A. D., et al. "Degradation of β-Lactam Antibiotics." Current Science, (2004) 87(12); 1684-1695.
Drugbank, Water solubility of Cefoxitin, Database accession No. DB01331, Accessed May 5, 2020; Retrieved from https://www.drugbank.ca/drugs/DB01331.
Drugbank, Water solubility of Cefpodoxime, Database accession No. DB01416, Accessed May 5, 2020; Retrieved from https://www.drugbank.ca/drugs/DB01416.
Sigma-Aldrich product webpage for LB Agar Ampicillin, Accessed May 5, 2020; Retrieved from https://www.sigmaaldrich.com/catalog/product/sigma/l5667?lang=en&region=US.
Sigma-Aldrich product webpage for LB Agar Carbenicillin, Accessed May 5, 2020; Retrieved from https://www.sigmaaldrich.com/catalog/product/sigma/l0418?lang=en&region=US.
Sigma-Aldrich product webpage for LB Broth (Miller), Accessed May 5, 2020; Retrieved from: https://www.sigmaaldrich.com/catalog/product/sigma/l2542?lang=en&region=US.
Teknova product webpage for LB Broth, Ampicillin, Accessed May 5, 2020; Retrieved from: https://www.teknova.com/b-broth-ampicillin-100.html.
ThermoFisher product webpage for LB Broth, Accessed May 5, 2020; Retrieved from: https://www.thermofisher.com/order/catalog/product/10855001.

* cited by examiner

BACTERIA CULTURE MEDIUM AND APPLICATIONS THEREOF

CROSS REFERENCE OF RELATED APPLICATION

This is a U.S. National Stage under 35 U.S.C 371 of the International Application PCT/CN2013/085254, filed Oct. 15, 2013, which claims priority under 35 U.S.C. 119(a-d) to CN 201310351748.1, filed Aug. 13, 2013.

BACKGROUND OF THE PRESENT INVENTION

Field of Invention

The present invention relates to a bacteria culture medium, especially to a culture medium for selective culturing bacteria with resistance to antibiotics.

Description of Related Arts

Selective culture medium is commonly used in biology and biomedical research and biological engineering. Antibiotics are often added into culture medium to kill or suppress the growth and reproduction of bacteria that are sensitive to antibiotics and selectively culture those bacteria with resistance to antibiotics from bacterial flora. Antibiotics are chemical substances being able to suppress bacteria growth or kill bacteria. Some bacteria are naturally resistant to certain antibiotics and can grow in selective culture medium containing these antibiotics. Bacteria that originally have no resistance to antibiotics can get antibiotics resistance by the adaption of genetic elements or gene mutations that can generate resistance to antibiotics. Such resistance is called adaptive resistance. The common antibiotics resistance genes are ampicillin resistance gene (ampr), tetracycline resistance gene (tetr), chloramphenicol resistance gene (Cmr, cat), kanamycin resistance gene (kanr) and neomycin resistance gene (neor). The ampicillin resistance gene is the most widely used selective marker gene in gene engineering. Most of plasmid vectors used in *E. coli* have ampicillin resistance gene. These bacteria are able to express this gene to generate resistance to ampicillin and thus can grow normally in presence of ampicillin.

Culture medium is nutrient substance supplied for microbes or animal and plant cells to grow, reproduce or accumulate metabolic products in the process of microbial fermentation or animal and plant cell culturing. The composition of culture medium includes carbon source, nitrogen source, mineral substances and other necessary ingredients such as the substances that cannot be synthesized by some organisms themselves, including some amino acids, vitamins or nucleotides, etc. Some pH buffering reagents are often added into culture medium to maintain a stable pH value. By chemical composition, culture medium can be divided into natural culture medium, complex culture medium and synthetic culture medium. All components of natural culture medium are natural products, such as animal, plant or microbial bodies including their extracts, etc. Complex culture medium consists of partial natural products and partial defined components. Synthetic culture medium consists of only defined components, for example, various combinations of pure chemicals. By physical form, culture medium is divided into solid culture medium, semi-solid culture medium and liquid culture medium, etc. By purpose, culture medium can also be divided into minimal culture medium, rich culture medium, differential culture medium and selective culture medium. Minimal culture medium provides the minimum nutrients. Rich culture medium contains more nutrient substances than minimal culture medium allowing microbe, animal and plant cell to grow faster. Differential culture medium is used to identify different types of microbe, animal and plant cells by special reactions of some premixed reagents during culturing. The selective culture medium is designed according to the special nutritional requirements of some organisms or their resistance to some chemical substances.

Selective culture medium is commonly used in biology and biomedical research and biological engineering. Antibiotics are often added into culture medium to kill or suppress the growth and reproduction of bacteria that are sensitive to antibiotics and selectively culture those bacteria with resistance to antibiotics from bacterial flora. Antibiotics are chemical substances which are able to suppress bacteria growth or kill bacteria. Some bacteria are naturally resistant to certain antibiotics and can grow in selective culture medium containing these antibiotics. Bacteria that originally have no resistance to antibiotics can get antibiotics resistance by the adaption of genetic elements or gene mutations that can generate resistance to antibiotics. Such resistance is called adaptive resistance. The common antibiotics resistance genes are ampicillin resistance gene (ampr), tetracycline resistance gene (tetr), chloramphenicol resistance gene (Cmr, cat), kanamycin resistance gene (kanr) and neomycin resistance gene (neor). The ampicillin resistance gene is the most widely used selective marker gene in gene engineering. Most of plasmid vectors used in *E. coli* have ampicillin resistance gene. These bacteria are able to express this gene to generate resistance to ampicillin and thus can grow normally in presence of ampicillin.

Ampicillin is a β-lactam antibiotic. Ampicillin inhibits bacterial cell wall synthesis and causes damage to the cell wall. As a result, these bacteria cells are killed or suppressed by ampicillin due to loss of the permeation barrier of the cell wall. The ampicillin resistance gene is actually a β-lactamase gene. The gene product, β-lactamase, can hydrolyze ampicillin and relieve its toxicity to bacteria cells. It was found that an enzyme from bacteria can damage penicillin before penicillin was used in large scale for first time. This was the first identified β-lactamase[1]. The ampicillin resistance gene used in molecular biology, bioengineering, biomedicine and industrial microbiology is bla gene, which encodes TEM-1 β-lactamase (TEM-1 β-lactamase). TEM-1 is the most common β-lactamase in bacteria, which was isolated from *Escherichia coli* and *Salmonella enterica* in 1960s[2]. In 1970s, $bla_{TEM-1}$ became widespread among Enterobacteriaceae, and by the early 1980s, it was the most prevalent resistance gene in clinical microbial populations throughout the world[3]. When classifying according to the gene sequence and protein sequence, TEM-1 belongs to Class A β-lactamase. This is the largest β-lactamase class that has been most researched. β-lactamases from this class were also called as "penicillinases" historically[4]. When classifying according to its function, TEM-1 belongs to Group 2b β-lactamase. TEM-1 can hydrolyze penicillin easily and also has certain ability to hydrolyze early cephalosporins (another major category of β-lactam antibiotics, the so-called the first generation of cephalosporins)[5,6].

Conventionally, the β-lactam antibiotic used to selectively culture the bacteria carrying bla gene is ampicillin. Therefore, bla gene is also called an ampicillin resistance gene. However, the TEM-1 β-lactamase encoded by bla gene can hydrolyze various other β-lactam antibiotics besides ampicillin. Scientists in Novagen suggested that carbenicillin could be used in place of ampicillin as a selective antibiotic[7]. Both ampicillin and carbenicillin are broad-spectrum penicillin which can efficiently kill Gram-positive bacteria and some Gram-negative bacteria including *E. coli*. *E. coli* widely used in modern biology, biological engineering, biomedicine and industrial microbiology is gram-negative bacterium. In culture medium, ampicillin and carbenicillinthe with a concentration of 100 µg/ml are often used to efficiently kill *E. coli* and other gram-negative bacteria without resistance, and grow *E. coli* with resistance to ampicillin normally.

β-lactam antibiotics are a big class of antibiotics which contain β-lactam ring in their molecular structures, including penicillin antibiotics, cephalosporin antibiotics and some non-typical β-lactam antibiotics. β-lactam antibiotics are organic acids. The β-lactam antibiotics solutions are acidic with a pH around 2-4. When they are practically used in body, the β-lactam antibiotics are usually transformed into their salts, such as sodium salts, potassium salts, etc., to accommodate to the pH required by organisms and increase their solubility. Therefore, the β-lactam antibiotics generally refer to their various salts in which the effective components are still the antibiotics themselves.

The core structure of β-lactam antibiotics, β-lactam ring, is a four-membered ring with high tension therein and is easy to open. In addition, its amido bond is susceptible to nucleophilic and electrophilic attack resulting in ring hydrolysis and opening. Therefore, although the dry powders of these pure antibiotics are stable, the stability of their solution is very poor. This is also the reason that all β-lactam antibiotic injections are in powder and are dissolved into solution immediately before use.

Ampicillin and carbenicillin also belong to β-lactam antibiotics. The medicine instruction for ampicillin indicates that the activity of the ampicillin dissolved in water or physiological saline (0.9% sodium chloride) will reduce by 10% in 2-3 days at 4° C. If it is dissolved in glucose injection solution, the activity of the ampicillin will reduce by 10% in around 1 hour even if it is kept at 4° C. This means that the stability of the ampicillin solution is very poor. As evidence in practice, the liquid culture medium and semi-solid agar culture plate medium containing ampicillin can generally be kept at 4° C. for only about one month. Only in few cases, the agar culture plate medium containing ampicillin is still useful after two months. Carbenicillin is more acid resistant than ampicillin. However, in a neutral pH condition of culture medium, its stability has no significant increase as compared with ampicillin. The shelf life of agar culture plate medium containing carbenicillin is also 1-2 months only. Within the range from −20° C. to 0° C., ampicillin becomes more unstable on the contrary and so do other β-lactam antibiotics[8,9]. Though a lower preservation temperature can extend the shelf life of β-lactam antibiotics in solution, the semi-solid culture medium represented by agar plate can only be stored above freezing point. This is because icing will make semi-solid agar culture plate medium crack or deform resulting in the influences of usage. The poor stability of β-lactam antibiotics in solution also limits the large-scale commercialization of the culture medium products premixed with these antibiotics. For example, the shelf life of the agar plate culture media premixed with ampicillin, ever supplied by Sigma-Aldrich, a famous chemical reagent company, were very short and only last 1-2 months. Some other companies also produce and supply such semi-solid agar plate culture media premixed with ampicillin, but all of them indicated clearly that the shelf life of these products were no more than 2 months and thus their production were very limited. If the culture medium premixed with β-lactam antibiotics can be stored stably for a long time, then large-scale commercialization of this product can be achieved and it will save a lot of operation time and increase the efficiency. However, there is no any research or report in this aspect to date.

To overcome the poor stability of β-lactam antibiotics in solution, people have developed some long lasting β-lactam antibiotics. These long lasting antibiotics mostly achieve long-time slow release action by reducing their solubility. These β-lactam antibiotics are exampled by procaine penicillin, benethamine penicillin, benzathine benzylpenicillin, cloxacillin benzathine and cephapirin benzathine, etc. Procaine penicillin (CAS: 54-35-3) is a procaine salt of penicillin, which is slightly soluble in water with a solubility around 4 mg/ml. Benethamine penicillin (CAS: 751-84-8) is a phenylethylbenzylamine salt of penicillin and the solubility in water is around 1 mg/ml. Benzathine benzylpenicillin (CAS: 1538-09-6), cloxacillin benzathine (CAS: 23736-58-5) and cephapirin benzathine (CAS: 97468-37-6) are dibenzylethylenediamine salts of penicillin, cloxacillin and cefapirin respectively and their solubility is lower, being around 50-200 µg/ml. As the very low solubility of these medicines, the undissolved medicine acts as storage pool and slowly releases with the dissolving to maintain a certain blood concentration for a long time after being injected into body as a form of suspension. In the suspension of these low soluble medicines, the part of medicine dissolved has reached a saturated concentration and the concentration is equal to their solubility. In human body, the medicine effect of procaine penicillin can last as many as 48 hours; the medicine effect of benzathine benzylpenicillin can last for 3-4 weeks. Cloxacillin benzathine and cephapirin benzathine are usually used as veterinary medicine and the medicine effect can also last for 3-4 weeks. In comparison, the medicine effects of normal β-lactam antibiotics in body can only last several hours. Besides, by reducing the solubility of medicine, the stability of medicine in a liquid can also be increased substantially. The components of such ready-to-use injection suspension named as Bicillin (trade name) are benzathine benzylpenicillin and procaine penicillin. Data shows that the injection suspension of benzathine cephapirin can be stored stably for as long as 36 months at less than 25° C.[10]. This indicates that the injection suspension of such medicines with low solubility can be stored stably. And normal β-lactam antibiotic injections can only be stored as powder. Long before, only those soluble antibiotics with high solubility were used as selective antibiotics in the culture medium for bacteria culturing. For years, there are neither researches on the feasibility of using such low soluble long lasting β-lactam antibiotics as selective antibiotics in culture medium nor data suggesting whether culture medium premixed with certain concentration of such low soluble long lasting β-lactam antibiotics shows an extended shelf life.

REFERENCES

[1] Abraham, E. P. and E. Chain, *An enzyme from bacteria able to destroy penicillin*. Nature, 1940.146(4): p. 837-8.

[2] Datta, N. and P. Kontomichalou, *Penicillinase synthesis controlled by infectious R factors in Enterobacteriaceae*. Nature, 1965.208(5007): p. 239-41.

[3] Medeiros, A. A., *Evolution and dissemination of beta-lactamases accelerated by generations of beta-lactam antibiotics*. Clin Infect Dis, 1997. 24 Suppl 1: p. S19-45.

[4] Ambler, R. P., *The structure of beta-lactamases*. Philos Trans R SocLond B BiolSci, 1980.289(1036): p. 321-31.

[5] Bush, K. and GA. Jacoby, *Updated functional classification of beta-lactamases*. Antimicrob Agents Chemother, 2010.54(3): p. 969-76.

[6] Bush, K., GA. Jacoby, and A. A. Medeiros, *A functional classification scheme for beta-lactamases and its correlation with molecular structure*. Antimicrob Agents Chemother, 1995.39(6): p. 1211-33.

[7]*pET System Manual* 11th Edition User Protocol TB055. 2011: Novagen.

[8] Concannon, J., et al., *Stability of aqueous solutions of amoxicillin sodium in the frozen andliquidstates*. Am J Hosp Pharm, 1986. 43(12): p. 3027-30.

[9] Savello, D. R. and R. F. Shangraw, *Stability of sodium ampicillin solutions in the frozen andliquidstates*. Am J Hosp Pharm, 1971. 28(10): p. 754-9.

[10]*Public Release Summary on Evaluation of the new active CEPHAPIRIN in the product/s MetricureBenzathine-cephapirin intra-uterine suspension.*, National Registration Authority for Agricultural and Veterinary Chemicals of Australia., 2001.

SUMMARY OF THE PRESENT INVENTION

The technical scheme of the present invention is designed to overcome the poor stability of β-lactam antibiotics or their salts after being premixed in culture medium and the very short shelf life of the selective culture medium premixed with conventional β-lactam antibiotics or their salts for culturing bacteria with resistance to β-lactam antibiotics.

A bacteria culture medium is provided. In common bacteria culture medium, one kind or several kinds of β-lactam antibiotics and/or the salts thereof are premixed. The β-lactam antibiotics and/or the salts thereof premixed in the bacteria culture medium are such β-lactam antibiotics and/or the salts thereof as having solubility in water greater than 0 mg/ml and less than 10 mg/ml at 25° C.

Further, the β-lactam antibiotics and/or the salts thereof are procaine penicillin, benethamine penicillin, benzathine benzylpenicillin, cloxacillin benzathineo or cephapirin benzathine.

Further, concentrations of the β-lactam antibiotics and/or the salts thereof premixed in the bacteria culture medium is greater than the solubility of the used β-lactam antibiotics and/or the salts thereof in water at 25° C. and less than 100 mg/ml.

The bacteria culture medium is used to selectively culture the bacteria with resistance to β-lactam antibiotics.

The present invention provides a culture medium premixed with β-lactam antibiotics that can be preserved for a long time. The culture media premixed with β-lactam antibiotics that can be preserved for a long time are used to selectively culture bacteria with resistance to β-lactam antibiotics in fields of modern biology, bioengineering, biomedicine and industrial microbiology, etc. The long preservation or long shelf life means that after preservation for a long time, the concentration of the β-lactam antibiotic in the culture medium is still within the range of effective working concentration. The effective working concentration of β-lactam antibiotics means that within such a concentration range, the β-lactam antibiotic in the culture medium can effectively suppress the growth of bacteria without resistance to β-lactam antibiotics, or effectively kill such bacteria without resistance to β-lactam antibiotics, or have both of the two effects concurrently. As a result, screening and culturing bacteria with resistance to β-lactam antibiotics can be achieved.

The shelf life of the culture medium of the present invention means the shelf life at a temperature above its freezing point and below 40° C. The freezing point of the culture medium containing different salts and mineral substances is usually lower than 0° C. In practical application, the convenient storage temperature is 0-30° C. and further, is 0-16° C. and the most commonly used storage temperature is 2-8° C. At the above storage temperatures, the shelf life of the culture medium of the present invention is much longer than that of traditional culture medium containing ampicillin and carbenicillin at the same temperature. Generally, the shelf life of culture medium of the present invention is greater than 6 months. Preferably, the shelf life is greater than 12 months. More preferably, the shelf life is greater than 24 months.

After long time storage, the culture medium of the present invention can be used normally without any adverse influences. After storage of 6 months, 12 months and 24 months, the performance of the culture medium premixed with β-lactam antibiotics on the bacteria growth speed, morphology, biological characteristics, genetic stability, etc. does not significantly change and have no adverse influences on conduct and efficiency of experiment or production operation. Specifically, the growth speed and viable count of the bacteria with resistance to β-lactam antibiotics at any culturing time point in the culture medium of the present invention that have been stored for the above mentioned time are not less than 70% of that in freshly prepared culture medium. Preferably, they are not less than 90% of that in freshly prepared culture medium. More preferably, they are 100% of that in freshly prepared culture medium.

The culture medium of the present invention is achieved by premixing β-lactam antibiotics in various bacteria culture media. Antibiotics are chemical substances being able to suppress bacteria growth or kill bacteria. The β-lactam antibiotics contain β-lactam ring, and the β-lactam ring is the active center for suppression and killing bacteria. The β-lactam antibiotics include penicillin antibiotics and its salts, cephalosporin antibiotics and its salts and all other non-typical β-lactam antibiotics and its salts.

The β-lactam antibiotics and its salts premixed in the culture medium of the present invention have a physical property of low solubility. The low solubility in the present invention means that the solubility in water at 25° C. is less than 10 mg/ml. Preferably, it is less than 1 mg/ml. More preferably, it is less than 0.25 mg/ml. The solubility of certain antibiotic in water can be determined by saturated concentration method. Specifically, a certain quality of (W1) of antibiotic is added in 100 ml water and dissolves sufficiently after stirring for over one hour at 25° C. Undissolved antibiotic (W2) is filtered out using a filter paper and weighed after drying. The solubility of this antibiotic is equal to W1-W2. The solubility of this antibiotic in water can also be determined by measuring the antibiotic saturation concentration of the filtered antibiotic solution. The β-lactam antibiotics concentration in solution can be determined by HPLC method and colorimetric method, etc. Such methods are widely used to determine the residual β-lactam antibiotics in food like milk, etc. The reagents, instruments and operating procedures used by these methods are publicly available. It is easy for the user to obtain this information. The culture medium of the present invention contains one or combination of several above mentioned β-lactam antibiotics and/or the salts thereof with low solubility. The concentration of the β-lactam antibiotics and/or the salts thereof premixed in the bacteria culture medium is greater than the solubility of the used β-lactam antibiotics and/or the salts thereof in water at 25° C. and less than 100 mg/ml. Preferably, it is less than 10 mg/ml. More preferably it is less than 1 mg/ml. Due to the different solubility of various β-lactam antibiotics and the salts thereof, the maximum amount of premixed β-lactam antibiotics and/or the salts thereof are also different. The amount of premixed β-lactam antibiotics and/or the salts thereof shall ensure that there are a part of undissolved antibiotics in the culture medium. The culture media achieve a long shelf life because the undissolved β-lactam antibiotics dissolved gradually and slowly. However, if the amounts of premixed β-lactam antibiotics are too much, the culture medium will become turbid and even viscous, and will also increase the cost. In the culture medium of the present invention, the β-lactam antibiotics and/or the salts thereof with a physical property of low solubility exist mostly as undissolved form and dissolve and release slowly so that the culture medium can maintain the β-lactam antibiotic at effective working concentration for more than 24 months. Significantly, the physical property of low solubility of these β-lactam antibiotics and its salts in the culture medium is the foundation for them to play a slow-release action and maintain an effective working concentration for a long time in the culture medium of the present invention. Therefore, any β-lactam antibiotics or the salts thereof with the low solubility in the culture medium are appropriate to be premixed into the culture medium to show a long term activity and give a long shelf life to the culture medium with these premixed low soluble β-lactam antibiotics.

DETAILED DESCRIPTION OF THE PREFERRED EMBODIMENT

Embodiment 1: Shelf Life Test of Ampicillin and Carbenicillin in Culture Medium

100 μg/ml, 1 mg/ml, 10 mg/ml and 100 mg/ml of ampicillin or carbenicillin were added into LB liquid culture medium (containing 1% tryptone, 0.5% yeast extract and 0.5% sodium chloride, pH=7.0) and LB agar plate culture medium (LB liquid culture medium plus 1.5% agar, pH=7.0). After two, three and four months of storage at 4° C., E. coli DH5α strain was inoculated into the culture media and incubated overnight at 37° C. Results showed that the culture media containing 100 μg/ml or 1 mg/ml ampicillin or carbenicillin were unable to suppress E. coli growth completely after two months of storage. The culture media containing 10 mg/ml ampicillin or carbenicillin were unable to suppress E. coli growth completely after three months of storage. The culture media containing 100 mg/ml ampicillin or carbenicillin were unable to suppress E. coli growth completely after four months of storage. The results indicate that shelf lives of conventionally used culture media containing 100 μg/ml ampicillin or carbenicillin are no more than two months. And increasing concentrations of two kinds of antibiotics is unable to significantly prolong the shelf life of the antibiotic activity in the culture medium.

Embodiment 2: Shelf Life Test of Procaine Penicillin in LB Culture Medium 10 mg/ml, 40 mg/ml and 80 mg/ml of procaine penicillin were added into LB liquid culture medium (containing 1% tryptone, 0.5% yeast extract and 0.5% sodium chloride, pH=7.0) and LB agar plate culture medium (LB liquid culture medium plus 1.5% agar, pH=7.0). After 6, 12, 18 and 24 months of storage at 4° C., E. coli DH5α strain was inoculated into the culture media and incubated overnight at 37° C. Results showed that all the culture media with the above concentrations of procaine penicillin were able to completely suppress the growth of E. coli DH5α strain after storage for the above periods. The results indicate that the procaine penicillin in the culture medium is still in a range of an effective working concentration.

Embodiment 3: Shelf Life Test of Procaine Penicillin in SOC Culture Medium 10 mg/ml, 40 mg/ml and 80 mg/ml of procaine penicillin were added into SOC liquid culture medium (containing 2% tryptone, 0.5% yeast extract and 0.05% sodium chloride, 2.5 mM potassium chloride and 10 mM magnesium chloride, pH=7.0) and SOC agar plate culture medium (SOC liquid culture medium plus 1.5% agar, pH=7.0). After 6, 12, 18 and 24 months of storage at 4° C., E. coli DH5α strain was inoculated into the culture media and incubated overnight at 37° C. Results showed that all the culture media with the above concentrations of procaine penicillin were able to completely suppress the growth of E. coli DH5α strain after storage for the above periods. The results indicate that the procaine penicillin in the culture medium is still in a range of an effective working concentration.

Embodiment 4: Shelf Life Test of Benethamine Penicillin in TB Culture Medium 5 mg/ml and 25 mg/ml of benethamine penicillin were added into TB liquid culture medium (containing 1.2% tryptone, 2.4% yeast extract, 0.5% glycerol, 17 mM potassium dihydrogen phosphate and 72 mM dipotassium hydrogen phosphate, pH=7.0) and TB agar plate culture medium (TB liquid culture medium plus 1.5% agar, pH=7.0). After 6, 12, 18 and 24 months of storage at 4° C., E. coli DH5α strain was inoculated into the culture media and incubated overnight at 37° C. Results showed that all the culture media with the above concentrations of benethamine penicillin were able to completely suppress the growth of E. coli DH5α strain after storage for the above periods. The results indicate that the benethamine penicillin in the culture medium is still in a range of an effective working concentration.

Embodiment 5: Shelf Life Test of Benethamine Penicillin in M9 Minimal Culture Medium 5 mg/ml and 25 mg/ml of benethamine penicillin were added into M9 minimal liquid culture medium (containing 48 mM disodium hydrogen phosphate, 22 mM potassium dihydrogen phosphate, 0.05% sodium chloride, 0.1% ammonia chloride, 2 mM magnesium sulfate, 0.1 mM calcium chloride and 0.2% glucose, pH=7.0) and M9 minimal agar plate culture medium (M9 minimal liquid culture medium plus 1.5% agar, pH=7.0). After 6, 12, 18 and 24 months of storage at 4° C., E. coli DH5α strain was inoculated into these culture media and incubated overnight at 37° C. Results showed that all the culture media with the above concentrations of benethamine penicillin were able to completely suppress the growth of E. coli DH5α strain after storage for the above periods. The results indicate that the benethamine penicillin in the culture medium is still in a range of an effective working concentration.

Embodiment 6: Shelf Life Test of Cloxacillin Benzathine in YT Culture Medium 0.5 mg/ml and 2.5 mg/ml of cloxacillin penicillin were added into YT liquid culture medium (containing 0.8% tryptone, 0.5% yeast extract and 0.25% sodium chloride, pH=7.0) and YT agar plate culture medium (YT liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of cloxacillin penicillin were able to completely suppress the growth of *E. coli* DH5α strain after storage for the above periods. The results indicate that the cloxacillin penicillin in the culture medium is still in a range of an effective working concentration.

Embodiment 7: Shelf Life Test of Cloxacillin Benzathine in YPD Culture Medium 0.5 mg/ml and 2.5 mg/ml of cloxacillin penicillin were added into YPD liquid culture medium (containing 2% tryptone, 1% yeast extract and 2% glucose, pH=7.0) and YPD agar plate culture medium (YPD liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of cloxacillin penicillin were able to completely suppress the growth of *E. coli* DH5α strain after storage for the above periods. The results indicate that the cloxacillin penicillin in the culture medium is still in a range of an effective working concentration.

Embodiment 8: Shelf Life Test of Benzathine Benzylpenicillin in LB Culture Medium 0.5 mg/ml and 2.5 mg/ml of benzathine benzylpenicillin were added into LB liquid culture medium (containing 1% tryptone, 0.5% yeast extract and 0.5% sodium chloride, pH=7.0) and LB agar plate culture medium (LB liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of benzathine benzylpenicillin were able to completely suppress the growth of *E. coli* DH5α strain after storage for the above periods. The results indicate that the benzathine benzylpenicillin in the culture medium is still in a range of an effective working concentration.

Embodiment 9: Shelf Life Test of Benzathine Benzylpenicillin in SOC Culture Medium 0.5 mg/ml and 2.5 mg/ml of benzathine benzylpenicillin were added into SOC liquid culture medium (containing 2% tryptone, 0.5% yeast extract and 0.05% sodium chloride, 2.5 mM potassium chloride and 10 mM magnesium chloride, pH=7.0) and SOC agar plate culture medium (SOC liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of benzathine benzylpenicillin were able to completely suppress the growth of *E. coli* DH5α strain after storage for the above periods. The results indicate that the benzathine benzylpenicillin in the culture medium is still in a range of an effective working concentration.

Embodiment 10: Shelf Life of Cephapirin Benzathine in YT Culture Medium 0.25 mg/ml and 1 mg/ml of cephapirin benzathine were added into YT liquid culture medium (containing 0.8% tryptone, 0.5% yeast extract and 0.25% sodium chloride, pH=7.0) and YT agar plate culture medium (YT liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of cephapirin benzathine were able to completely suppress the growth of *E. coli* DH5α strain after storage for the above periods. The results indicate that the b cephapirin benzathine in the culture medium is still in a range of an effective working concentration.

Embodiment 11: Shelf Life of Cephapirin Benzathinein M9 Minimal Culture Medium 0.25 mg/ml and 1 mg/ml of cephapirin benzathine were added into M9 minimal liquid culture medium (containing 48 mM disodium hydrogen phosphate, 22 mM potassium dihydrogen phosphate, 0.05% sodium chloride, 0.1% ammonia chloride, 2 mM magnesium sulfate, 0.1 mM calcium chloride and 0.2% glucose, pH=7.0) and M9 minimal agar plate culture medium (M9 minimal liquid culture medium plus 1.5% agar, pH=7.0). After 6, 12, 18 and 24 months of storage at 4° C., *E. coli* DH5α strain was inoculated into these culture media and incubated overnight at 37° C. Results showed that all the culture media with the above concentrations of cephapirin benzathine were able to completely suppress the growth of *E. coli* DH5α strain after storage for the above periods. The results indicate that the b cephapirin benzathine in the culture medium is still in a range of an effective working concentration.

Embodiment 12: Shelf Life Test of Mixture of Procaine Penicillin and Cloxacillin Benzathine in Culture Medium 25 mg/ml of procaine penicillin and 2.5 mg/ml of cloxacillin benzathine were added into LB liquid culture medium (containing 1% tryptone, 0.5% yeast extract and 0.5% sodium chloride, pH=7.0) and LB agar plate culture medium (LB liquid culture medium plus 1.5% agar, pH=7.0). After 6, 12, 18 and 24 months of storage at 4° C., *E. coli* DH5α strain was inoculated into the culture medium and incubated overnight at 37° C. Results showed that the culture medium with mixture of procaine penicillin and cloxacillin benzathine was able to completely suppress the growth of *E. coli* DH5α strain after storage for the above periods. The results indicate that the antibiotics mixture in the culture medium is still in a range of an effective working concentration.

Embodiment 13: Shelf Life of Mixture of Procaine Penicillin, Benethamine Penicillin, Benzathine Benzyl Penicillin and Cephapirin Benzathine in Culture Medium 50 mg/ml of procaine penicillin, 5 mg/ml of benethamine penicillin, 1 mg/ml of benzathine benzylpenicillin and 0.5 mg/ml of cephapirin benzathine were added into LB liquid culture medium (containing 1% tryptone, 0.5% yeast extract and 0.5% sodium chloride, pH=7.0) and LB agar plate culture medium (LB liquid culture medium plus 1.5% agar, pH=7.0). After 6, 12, 18 and 24 months of storage at 4° C., *E. coli* DH5α strain was inoculated into the culture medium and incubated overnight at 37° C. Results showed that the culture medium with antibiotics mixture was able to completely suppress the growth of *E. coli* DH5α strain after storage for the above periods. The results indicate that the antibiotics mixture in the culture medium is still in a range of an effective working concentration.

Embodiment 14: The Influence of Gamma-Ray Irradiation Sterilization on the Shelf Life of the Culture Medium Containing β-Lactam Antibiotics The liquid culture medium and agar plate culture medium premixed with β-lactam antibiotics in Embodiments 2-13 were irradiated by Co-60 gamma-ray for sterilization treatment. The irradiation dosage was 30 KGy which is higher than the medical level irradiation dosage of 25 KGy and is sufficient to ensure SAL<10-6. After gamma-ray irradiation, these culture media were stored at 4° C. for 6, 12, 18 and 24 months. After storage, these culture media were subject to shelf life testing as above. Results showed that the shelf lives of all culture media irradiated by gamma-ray have no differences with those of culture media without gamma-ray irradiation. After storage for the above periods, the irradiated culture media premixed with β-lactam antibiotics as Embodiments 2-13 were able to completely suppress the growth of *E. coli* DH5α strain. The results indicate that the antibiotics in the culture media were still in a range of an effective working concentration.

What is claimed is:

1. A bacteria culture medium comprising a β-lactam antibiotic or salt thereof dissolved in water,
    wherein the amount of the β-lactam antibiotic or salt thereof (in mg) per unit volume of the bacterial culture medium (in ml) is greater than the solubility of the β-lactam antibiotic or salt thereof in water at 25° C. and less than 10 mg/ml and does not render the bacteria culture medium turbid or viscous; and
    wherein the β-lactam antibiotic is selected from the group consisting of benzathine benzylpenicillin, cloxacillin benzathine, and cephapirin benzathine.

2. The bacteria culture medium of claim 1, wherein the bacteria culture medium is a liquid culture medium.

3. A bacteria culture medium comprising a β-lactam antibiotic or salt thereof dissolved in water,
    wherein the amount of the β-lactam antibiotic or salt thereof (in mg) per unit volume of the bacterial culture medium (in ml) is greater than the solubility of the β-lactam antibiotic or salt thereof in water at 25° C. and less than 1 mg/ml and does not render the bacteria culture medium turbid or viscous; and
    wherein the β-lactam antibiotic is selected from the group consisting of benzathine benzylpenicillin, cloxacillin benzathine, and cephapirin benzathine.

4. The bacteria culture medium of claim 3, wherein the bacteria culture medium is a liquid culture medium.

5. The bacteria culture medium of claim 1, wherein the β-lactam antibiotic or salt thereof is benzathine benzylpenicillin.

6. The bacteria culture medium of claim 1, wherein the β-lactam antibiotic or salt thereof is cloxacillin benzathine or cephapirin benzathine.

7. The bacteria culture medium of claim 1, wherein the bacteria culture medium is a semi-solid culture medium.

8. The bacteria culture medium of claim 1, wherein the solubility of the β-lactam antibiotic or salt thereof in water at 25° C. is less than 0.25 mg/ml.

9. The bacteria culture medium of claim 1, wherein the solubility of the β-lactam antibiotic or salt thereof in water at 25° C. is 50-200 μg/ml.

10. A method of selectively culturing β-lactam antibiotic resistant bacteria, comprising:
    inoculating the bacteria culture medium of claim 1 with bacteria, thereby selectively culturing β-lactam antibiotic resistant bacteria in the bacteria culture medium while killing or suppressing bacteria that are sensitive to the β-lactam antibiotic or salt thereof.

11. A method of selectively culturing β-lactam antibiotic resistant bacteria, comprising:
    inoculating the bacteria culture medium of claim 1 with bacteria, thereby selectively culturing β-lactam antibiotic resistant bacteria in the bacteria culture medium while killing or suppressing bacteria that are sensitive to the β-lactam antibiotic or salt thereof,
    wherein the bacteria culture medium has been stored at 0-16° C. for six months or more prior to the inoculating step.

12. The method of claim 11, wherein the bacteria culture medium has been stored at 2-8° C. for 12 months or more prior to the inoculating step,
    wherein the bacteria culture medium has been stored at 4° C. for 18 months or more prior to the inoculating step, or
    wherein the bacteria culture medium has been stored at 4° C. for about 24 months prior to the inoculating step.

13. The bacteria culture medium of claim 1, wherein the amount of the β-lactam antibiotic or salt thereof (in mg) per unit volume of the bacterial culture medium (in ml) is 0.5 mg/ml.

14. The bacteria culture medium of claim 1, wherein the bacteria culture medium is irradiated with gramma irradiation and has a temperature of 4° C.

* * * * *